United States Patent
Wollweber et al.

[11] Patent Number: 5,091,408
[45] Date of Patent: Feb. 25, 1992

[54] FUNGICIDAL 3-CYANO-4-PHENYL-PYRROLES

[75] Inventors: Detlef Wollweber, Wuppertal; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 506,414

[22] Filed: Apr. 6, 1990

[30] Foreign Application Priority Data

Apr. 13, 1989 [DE] Fed. Rep. of Germany ....... 3912156

[51] Int. Cl.⁵ .................. C07D 207/34; A01N 43/36
[52] U.S. Cl. .................................. 514/427; 548/561
[58] Field of Search ............... 548/566, 561; 514/429, 514/427

[56] References Cited

U.S. PATENT DOCUMENTS

| | | | |
|---|---|---|---|
| 4,680,413 | 7/1987 | Genda et al. | 548/561 X |
| 4,705,801 | 11/1987 | Martin et al. | 548/561 X |
| 4,812,580 | 3/1989 | Martin | 548/561 |
| 4,912,229 | 3/1990 | Wollweber | 548/561 X |
| 4,952,601 | 8/1990 | Wollweber et al. | 548/561 X |
| 4,960,789 | 10/1990 | Wollweber et al. | 548/561 X |

FOREIGN PATENT DOCUMENTS 0182738 5/1986 European Pat. Off. .
0236272 9/1987 European Pat. Off. .
0310558 4/1989 European Pat. Off. .
0315869 5/1989 European Pat. Off. .
0318704 6/1989 European Pat. Off. .
1193498 5/1965 Fed. Rep. of Germany .
2927480 1/1980 Fed. Rep. of Germany .

*Primary Examiner*—Joseph Paul Brust
*Attorney, Agent, or Firm*—Sprung Horn Kramer & Woods

[57] ABSTRACT

Fungicidal 3-cyano-4-phenyl-pyrroles of the formula

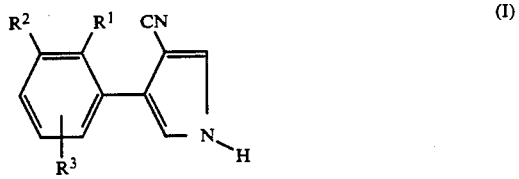

in which
R¹ represents chlorine, bromine, alkyl, halogenoalkyl or halogenoalkoxy,
R² represents chlorine, bromine, alkyl, halogenoalkyl or halogenoalkoxy and
R³ represents hydrogen or fluorine,
with the proviso that at least one of the radicals R¹ or R² represents halogenoalkyl.

6 Claims, No Drawings

FUNGICIDAL 3-CYANO-4-PHENYL-PYRROLES

The invention relates to new 3-cyano-4-pyrrole derivatives, to a process for their preparation, to their use for combating pests, in particular as fungicides, and to new intermediates.

It has been disclosed that certain 3-cyano-4-phenyl-pyrroles, such as, for example, the compound 3-cyano-4-(2,3-dichlorophenyl)-pyrrole, have fungicidal activity (cf., for example, EP 236,272).

Furthermore, it is known that certain perhalogenoalkylmercapto-sulphonamides and -sulphamides, such as, for example, N,N-dimethyl-N'-phenyl-N'-(fluorodichloromethylthio)-sulphamide, have fungicidal properties (cf. DAS 1,193,498).

However, the activity of these previously disclosed compounds is not completely satisfactory in all areas of application, in particular at low application rates and concentrations.

New 3-cyano-4-phenyl-pyrrole derivatives of the general formula (I),

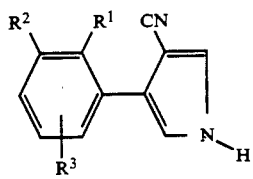

in which
$R^1$ represents chlorine, bromine, alkyl, halogenoalkyl or halogenoalkoxy,
$R^2$ represents chlorine, bromine, alkyl, halogenoalkyl or halogenoalkoxy and
$R^3$ represents hydrogen or fluorine, with the proviso that at least one of the radicals $R^1$ or $R^2$ represents halogenoalkyl, have been found.

Furthermore, it has been found that the new 3-cyano-4-phenyl-pyrroles of the general formula (I)

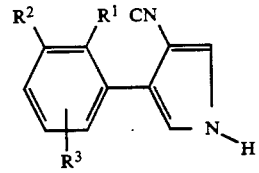

in which
$R^1$ represents chlorine, bromine, alkyl, halogenoalkyl or halogenoalkoxy,
$R^2$ represents chlorine, bromine, alkyl, halogenoalkyl or halogenoalkoxy and
$R^3$ represents hydrogen or fluorine,
with the proviso that at least one of the radicals $R^1$ or $R^2$ represents halogenoalkyl, are obtained when substituted cinnamonitriles of the formula (II)

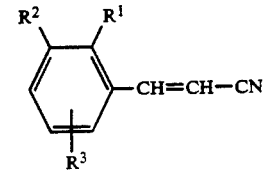

in which $R^1$, $R^2$ and $R^3$ have the abovementioned meanings, are reacted with sulphonylmethyl isocyanides of the formula (III),

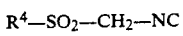

$$R^4-SO_2-CH_2-NC \qquad (III)$$

in which
$R^4$ represents alkyl or optionally substituted aryl, in the presence of a base and if appropriate in the presence of a diluent.

Finally, it has been found that the new 3-cyano-4-phenyl-pyrroles of the general formula (I) have a good action against pests.

Surprisingly, the 3-cyano-4-phenyl-pyrroles of the general formula (I) according to the invention show a considerably better fungicidal activity than, for example, the 3-cyano-4-phenyl-pyrroles and perhalogenoalkylmercapto-sulphonamides and -sulphamides known from the prior art, such as 3-cyano-4-(2,3-dichlorophenyl)pyrrole and N,N-dimethyl-N'-phenyl-N'-(fluorodichloromethylthio)-sulphamide, which are closely related compounds chemically and with respect to their action.

Preferred substituents or ranges of the radicals shown in the formulae mentioned above and below are illustrated in the following:

In the general formulae, alkyl in general denotes straight-chain or branched alkyl having 1 to 6 carbon atoms, preferably having 1 to 4 and particularly preferably having 1 or 2 carbon atoms; examples which may be mentioned are methyl, ethyl, n- and i-propyl, n-, i-, s- and t-butyl, pentyl and hexyl.

Halogenoalkyl and halogenoalkoxy, as substituents in the radicals, in general represent straight-chain or branched radicals each having 1 to 4 carbon atoms, particularly preferably having 1 or 2 carbon atoms and in each case having 1 to 9, or 1 to 5, identical or different halogen atoms as defined under halogen; examples which may be mentioned are: fluoromethyl, chloromethyl, bromomethyl, fluoroethyl, chloroethyl, bromoethyl, fluoro-n-propyl, chloro-n-propyl, difluoromethyl, tri-fluoromethyl, dichloromethyl, trichloromethyl, difluoroethyl, trifluoroethyl, trichloroethyl, chloro-difluoromethyl, trifluoro-chloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy and trifluorochloroethoxy, trifluoromethyl and trifluoromethoxy being particularly emphasized.

Halogen in the definitions of halogenoalkyl and halogenoalkoxy represents fluorine, chlorine, bromine and/or iodine, in particular fluorine, chlorine and/or bromine and particularly fluorine or chlorine.

Formula (I) provides the general definition of the 3-cyano-4-phenyl-pyrroles according to the invention. Preferred compounds of the formula (I) are those in which
$R^1$ represents chlorine, bromine, straight-chain or branched alkyl having 1 to 4 carbon atoms or in each case straight-chain or branched halogenoalkyl or halogenoalkoxy in each case having 1 to 4 carbon atoms and 1 to 9 identical or different halogen atoms, $R^2$ represents chlorine, bromine, straight-chain or branched alkyl having 1 to 4 carbon atoms or in each case straight-chain or branched halogenoalkyl or halogenoalkoxy in each case having 1 to 4 carbon atoms and 1 to 9 identical or different halogen atoms and $R^3$ represents hydrogen or fluorine, with the proviso that at least one of the radicals $R^1$ or $R^2$ represents halogenoalkyl.

Particularly preferred compounds of the formula (I) are those in which $R^1$ represents chlorine, bromine, methyl, ethyl, trifluoromethyl or trifluoromethoxy, $R^2$ represents chlorine, bromine, methyl, ethyl, trifluoromethyl or trifluoromethoxy and $R^3$ represents hydrogen or fluorine, with the proviso that at least one of the radicals R or $R^2$ represents trifluoromethyl.

Very particularly preferred compounds of the formula (I) which may be mentioned are: 3-cyano-4-(2-methyl-3-trifluoromethylphenyl)-pyrrole and 3-cyano-4-(2,3-di-trifluoromethylphenyl)pyrrole.

The preferred definitions indicated for the compounds of the formula (I) also apply to the starting compounds of the formula (II).

The following 3-cyano-4-phenyl-pyrroles of the general formula (I) may be mentioned individually in addition to the compounds mentioned in the preparation examples:

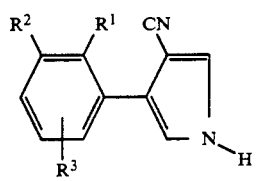

TABLE 1

| $R^1$ | $R^2$ | $R^3$ |
|---|---|---|
| $CF_3$ | Cl | H |
| $CF_3$ | $CH_3$ | H |
| $CF_3$ | $OCF_3$ | H |
| $CF_3$ | Br | H |
| Cl | $CF_3$ | H |
| Br | $CF_3$ | H |
| $OCF_3$ | $CF_3$ | H |
| $CF_3$ | Cl | 4F |
| $CF_3$ | Cl | 5F |
| $CF_3$ | $CH_3$ | 4F |
| $CF_3$ | $CH_3$ | 5F |
| $CF_3$ | $OCF_3$ | 4F |
| $CF_3$ | $OCF_3$ | 5F |
| Cl | $CF_3$ | 4F |
| Cl | $CF_3$ | 5F |
| Br | $CF_3$ | 4F |
| Br | $CF_3$ | 5F |
| $OCF_3$ | $CF_3$ | 4F |
| $OCF_3$ | $CF_3$ | 5F |
| $CH_3$ | $CF_3$ | 4F |
| $CH_3$ | $CF_3$ | 5F |

If, for example, 2-methyl-3-trifluoromethyl cinnamonitrile and p-toluenesulphonylmethyl isocyanide are used as starting substances and sodium hydride as the base, the course of the reaction of the process according to the invention can be represented by the following equation:

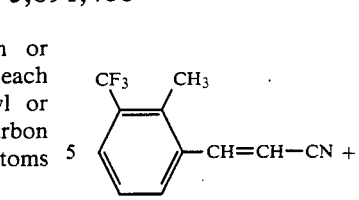

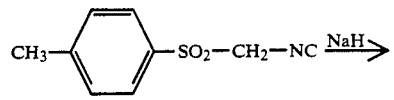

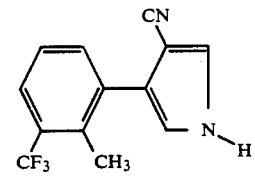

Formula (II) provides a general definition of the substituted cinnamonitriles required as starting substances for carrying out the process according to the invention. In this formula (II), $R^1$, $R^2$ and $R^3$ preferably represent those radicals which have already been mentioned as preferred for these substituents in connection with the description of the substances of the formula (I) according to the invention.

The substituted cinnamonitriles of the formula (II) are new. However, they are obtained in analogy to known methods (cf., for example, DE-OS (German Published Specification) 2,927,480), for example when a) anilines of the formula (IV)

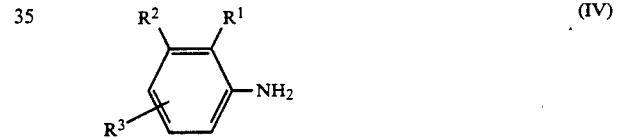

in which $R^1$, $R^2$ and $R^3$ have the abovementioned meanings, with the proviso that at least one of the radicals $R^1$ or $R^2$ represents halogenoalkyl, are reacted in a first step with acrylonitrile under customary diazotization conditions, for example in the presence of sodium nitrite and hydrochloric acid, and in the presence of a suitable metal salt catalyst, such as, for example, copper(II) chloride or copper(II) oxide, and if appropriate in the presence of a suitable diluent, such as, for example, acetone or water, at temperatures between −20° C. and 50° C. ("Meerwein arylation"; cf. also here Organic Reactions 11, 189 [1960]; Organic Reactions 24. 225 [1976] or C. Ferri in "Reaktionen der organischen Synthese" (Reactions of organic synthesis) p. 319, Thieme Verlag Stuttgart 1978) and then in a second step dehydrohalogenating the substituted α-chloro-β-phenylpropionitriles thus obtained of the formula (V)

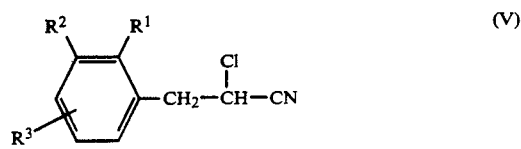

in which $R^1$, $R^2$ and $R^3$ have the abovementioned meanings, with the proviso that at least one of the radicals $R^1$ or $R^2$ represents halogenoalkyl, with bases, such as, for example triethylamine or diazabicycloundecene, in a customary manner, if appropriate in the presence of a diluent, such as, for example, tetrahydrofuran, at temperatures between 0° C. and 50° C. (cf. also the preparation examples) or alternatively when b) benzaldehydes of the formula (VI)

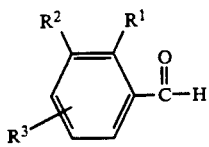

in which $R^1$, $R^2$ and $R^3$ have the abovementioned meanings, with the proviso that at least one of the radicals $R^1$ or $R^2$ represents halogenoalkyl, are condensed with cyanoacetic acid of the formula (VII)

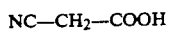    (VII)

and simultaneously decarboxylated in a customary manner in the presence of a base, such as, for example, piperidine or pyridine, and if appropriate in the presence of a suitable diluent, such as, for example, pyridine, at temperatures between 50° C. and 120° C. (cf., for example, "Organikum" p. 571/572; 15th edition; VEB Deutscher Verlag der Wissenschaften Berlin 1981 and also the Preparation Examples).

The anilines of the formula (IV) are known in some cases (cf., for example, DE-OS (German Published Specification) 3,726,891, JP 62,298,562, EP-OS 206,951, JP 61,083,146) or are obtainable in analogy to known methods.

The benzaldehydes of the formula (VI) required as precursors for the preparation of the new starting products of the formula (II) according to variant b) are for the most part known (cf., for example, EP 225,175, EP 125,803, EP 174,131, EP 169,009, EP 168,151, EP 145,334, U.S. Pat. No. 4,572,909, JP 84,118,782, J. Chem. Soc., Perkin Trans. 1, 1837-1844 and J. Med. Chem. 29, 1696-1702). Cyanoacetic acid of the formula (VII) is also a generally known compound of organic chemistry.

Formula (III) provides a general definition of the sulphonylmethyl isocyanides furthermore required as starting substances for carrying out the process according to the invention. In this formula (III), $R^4$ preferably represents alkyl having 1 to 4 carbon atoms, particularly preferably methyl or optionally monosubstituted phenyl, such as, for example, 4-methylphenyl or 4-chlorophenyl, or phenyl.

The sulphonylmethyl isocyanides of the formula (III) are known (cf., for example, Synthesis 1985, 400–402; Org. Syntheses 57, 102-106 [1977]; J. org. Chem. 42, 1153-1159 [1977]; Tetrahedron Lett. 1972, 2367-2368).

Possible diluents for carrying out the process according to the invention are inert organic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahdyrofuran or ethylene glycol dimethyl ether or ethylene glycol diethyl ether, amides, such as dimethylformamide, dimethylacetamide, N-methylformanilide, N-methylpyrrolidone or hexamethylphosphoramide, or sulphoxides, such as dimethyl sulphoxide.

The process according to the invention can optionally also be carried out in a two-phase system, such as, for example, water/toluene or water/dichloromethane, if appropriate in the presence of a phase-transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyldimethyl-ammonium methylsulphate, dimethyl-$C_{12}$/$C_{14}$-alkylbenzylammonium chloride, tetrabutylammonium hydroxide, 15-crown-5, 18-crown-6, triethylbenzylammonium chloride and trimethylbenzylammonium chloride.

The process according to the invention is preferably carried out in the presence of a suitable base. Those which are suitable are all customarily utilizable inorganic and organic bases. Hydrides, hydroxides, amides, alkoxides, carbonates or hydrogen carbonates of alkali metals, such as, for example, sodium hydride, sodium amide, sodium hydroxide, sodium methoxide, sodium ethoxide, potassium t-butoxide, sodium carbonate or sodium hydrogen carbonate and also tertiary amines, such as, for example, triethylamine, N,N-dimethylaniline, pyridine, N,N-dimethylaminopyridine, diazabicyclooctane (DABCO), diazabicyclononene (DBN) or diazabicycloundecene (DBU) are preferably used.

The reaction temperatures can be varied within a relatively wide range when carrying out the process according to the invention. In general, the reaction is carried out at temperatures between $-30°$ C. and $+120°$ C., preferably at temperatures between $-20°$ C. and $+50°$ C.

For carrying out the process according to the invention, 1.0 to 2.0 moles, preferably 1.0 to 1.5 moles, of sulphonylmethyl isocyanide of the formula (III) and 1.0 to 2.0 moles, preferably 1.0 to 1.5 moles, of base are in general employed per mole of substituted cinnamonitrile of the formula (II).

In this connection, it may be advantageous to carry out the reaction in the presence of a protective gas atmosphere such as, for example, argon. The reaction is carried out, and the reaction products are worked up and isolated by generally customary methods.

Alternatively to the preparation of the active compounds according to the invention with the aid of the preparation process according to the invention, various other preparation processes for the preparation of the active compounds according to the invention are conceivable.

Thus, active compounds of the formula (I) according to the invention are also obtained, for example, when α-cyanocinnamic acid esters are reacted with p-toluenesulphonylmethyl isocyanide in the presence of bases and in the presence of copper(II) salts (cf. J6-1030-571 or J6-1200-984) or when α-substituted cinnamonitriles are cyclized with isocyanoacetic acid esters in the presence of sodium hydride, and the pyrrole-2-carboxylic acid esters thus obtained are hydrolyzed with bases and then thermally decarboxylated (cf. JP 59/212,468) or when phenacylamine derivatives are reacted with suitably substituted acrylonitrile derivatives (cf. EP 174,910) or when 3-trifluoromethyl-4-phenyl-pyrroles are reacted with ammonia at elevated temperature and elevated pressure (cf EP 182,738) or when 3-cyano-4-phenyl-$\Delta^2$-pyrrolines are oxidized in the presence of copper(II) salts or iron(III) salts (cf. EP 183,217) or when α-cyanoacrylic acid derivatives are reacted with isocyanoacetic acid esters in the presence of a base and the Δ²-pyrroline-2-carboxylic acid derivatives thus obtained are oxidatively decarboxylated in a second step in the presence of a base and in the presence of a metal salt catalyst (cf. German Patent Application P 3,718,375 of 02.06.1987).

The active compounds according to the invention have a strong action against pests and can be employed practically for combating undesired injurious organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:
Pythium species, such as, for example, *Pythium ultimum*; Phytophthora species, such as, for example, *Phytophthora infestans*;
Pseudoperonospora species, such as, for example, *Pseudoeronospora humuli* or *Pseudoperonospora cubensis*;
Plasmopara species, such as, for example, *Plasmopara viticola*;
Peronospora species, such as, for example, *Peronospora pisi* or *P. brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus*;
Puccinia species, such as, for example, *Puccinia recondita*;
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae* and
Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be employed here with particularly good effect for combating diseases in fruit and vegetable cultivation, such as, for example, against the causative organism of brownish-grey mildew of beans (*Botrytis cinerea*) or for combating rice diseases such as, for example, against the causative organism of rotten neck of rice (Pyricularia oryzae) or against *Erysiphe graminis* on barley.

Furthermore, some of the active compounds according to the invention show good fungicidal actions against Venturia on apple, Pellicularia on rice, Leptosphaeria, Cochliobolus, Pyrenophora and Fusarium on cereal cultures. In addition, some of the active compounds according to the invention also show a good in vitro action.

Depending on their individual physical and/or chemical properties, the active compounds can be converted into the customary formulations, such as solutions, emulsions, suspensions, powders, foams, pastes, granules, aerosols, very fine capsules in polymeric substances and in coating compositions for seed, as well as ULV cold and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For treatment of the soil, active compound concentrations of 0.00001 to 0.1% by weight, preferably 0.0001 to 0.02% by weight, are required at the place of action.

PREPARATION EXAMPLES

Example 1

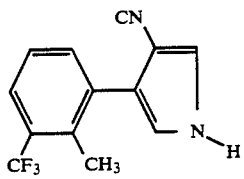

A solution of 5.0 g (0.0237 mol) of 3-(2-methyl-3-trifluoromethyl-phenyl)-acrylonitrile and 6.0 g (0.0308 mol) of p-toluenesulphonylmethyl isocyanide in 20 ml of a mixture of tetrahydrofuran/dimethyl sulphoxide (6:1) is added dropwise at −10° C. to −20° C. with stirring to 1.0 g (0.033 mol) of sodium hydride (80% strength in mineral oil) in 17.0 ml of tetrahydrofuran under an argon atmosphere. After completion of the addition, the reaction mixture is allowed to come to room temperature, water is added, the mixture is extracted several times with ethyl acetate, and the combined ethyl acetate phases are washed with water, dried over sodium sulphate and concentrated in vacuo. The residue is purified by chromatography on silica gel (eluent: cyclohexane/ethyl acetate 5:1).

4.5 g (76% of theory) of 3-cyano-4-(2-methyl-3-trifluoromethylphenyl)-pyrrole of melting point 99° C.-100° C. are obtained.

Example 2

3-Cyano-4-(2,3-di-trifluoromethyl-phenyl)-pyrrole of melting point 147° C.-149° C. is obtained in an analogous manner to Example 1 and with consideration for the instructions in the description of the process according to the invention.

PREPARATION OF THE STARTING COMPOUNDS

Example II-1

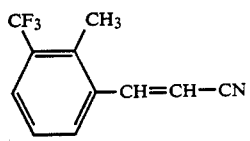

14.4 g (0.094 mol) of diazabicycloundecene are added dropwise at room temperature with stirring to 21.2 g (0.086 mol) of 2-chloro-3-(2-methyl-3-trifluoromethylphenyl)-propionitrile in 120 ml of tetrahydrofuran, the mixture is stirred at room temperature for 15 hours after completion of the addition and filtered, the filtrate is concentrated in vacuo, the residue is taken up in ethyl acetate, washed successively with 1 normal hydrochloric acid and water and dried over sodium sulphate, and the solvent is removed in vacuo.

After distillation in a bulb tube distillation apparatus, 7.9 g (44% of theory) of 3-(2-methyl-3-trifluoromethylphenyl)-acrylonitrile of melting point 87° C.-88° C. are obtained.

Example II-2

3-(2,3.Di-trifluoromethyl-phenyl)-acrylonitrile is obtained in an analogous manner to Example (II-1) and according to the general instructions for the preparation. The $^1$H-NMR spectra (CDCl$_3$) $\delta$ = 5.7-5.9 1H (dd, dd)ppm were recorded in deuterochloroform (CDCl$_3$) using tetramethylsilane (TMS) as an internal standard. The chemical shift is indicated as the $\delta$ value in ppm.

Example V-1

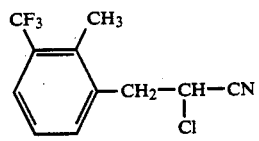

20 mol of concentrated hydrochloric acid is added at 0°-5° C. to a suspension of 16.7 g of 2-methyl-3-trifluoromethylaniline (0.095 mol) in 50 ml of water and the mixture is then briefly warmed to 60°-80° C. until a clear solution has formed. The solution is cooled very rapidly to 0°-5° C. with vigorous stirring, 22.4 ml (0.286 mol) of acrylonitrile are added dropwise to the fine suspension at 0°-5° C. and a solution of 6.75 g of sodium nitrite in 10 ml of water is then rapidly added, and the mixture is kept at 5° C. for a further 5 minutes and stirred at 20° C. for 1 hour. After cooling, 0.8 g of copper(II) oxide powder is added to the reaction mixture at 0°–10° C. in portions, a vigorous evolution of nitrogen gas occurring. After completion of the evolution of gas, the mixture is stirred for a further 2 hours at 0°–10° C., then for 15 hours at room temperature, dichloromethane is added, and the mixture is washed with water, dried over sodium sulphate and concentrated in vacuo. 21.2 g (90% of theory) of 2-chloro-3-(2-methyl-3-trifluoromethylphenyl)-propionitrile are obtained as a brown oil.

M/e 247 (+), 228, 212, 173 (100%)

Example V-2

2-Chloro-3-(2,3-di-trifluoromethyl-phenyl)propionitrile is obtained in an analogous manner to Example (V-1) and according to the general instructions for the preparation.

M/e 301 (M+), 282, 246, 227 (100%), 177.

Use Examples

The compounds shown below were employed as comparison substances in the following Use Examples:

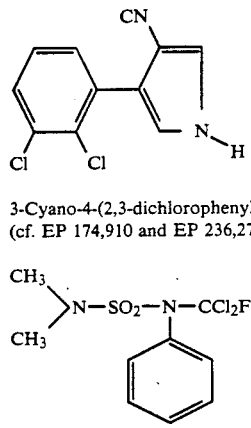
(A)

3-Cyano-4-(2,3-dichlorophenyl)-pyrrole
(cf. EP 174,910 and EP 236,272).

(B)

$$\begin{array}{c}CH_3\\ \phantom{C}\\ CH_3\end{array}\!\!\!\!>\!\!N\!-\!SO_2\!-\!N\!-\!CCl_2F$$
with N-phenyl group N,N-dimethyl-N'-phenyl-N'-(fluorodichloromethylthio)-sulphamide (known from D.A.S. 1,193,498).

Example A

| Botrytis test (dwarf beans)/protective | |
|---|---|
| Solvent: | 4.7 parts by weight of acetone |
| Emulsifier: | 0.3 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, for example, the compound according to Preparation Example 1 shows a clearly superior action compared to the prior art.

Example B

| Pyricularia test (rice)/protective | |
|---|---|
| Solvent: | 12.5 parts by weight of acetone |
| Emulsifier: | 0.3 parts by weight of alkylaryl polyglycol ether |

To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, for example, the compound according to Preparation Example 1 shows a clearly superior action compared to the prior art.

Example C

| Erysiphe test (barley)/protective | |
|---|---|
| Solvent: | 100 parts by weight of dimethyl formamide |
| Emulsifier: | 0.25 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, for example, the compound according to Preparation Example 1 shows a clearly superior action compared to the prior art.

It is understood that the specification and examples are illustrative but not limitative of the present invention and that other embodiments within the spirit and scope of the invention will suggest themselves to those skilled in the art.

We claim:

1. A 3-cyano-4-pyrrole of the formula

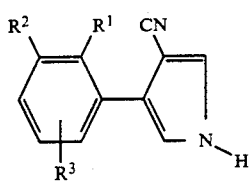 (I)

in which
one of $R^1$ and $R^2$ is $CF_3$ and the other is alkyl having 1 to 4 carbon atoms or $CF_3$, and
$R^3$ is H or F.

2. A compound according t claim 1, in which one of $R^1$ and $R^2$ is $CF_3$ and the other is methyl or ethyl.

3. A compound according to claim 1, wherein such compound is 3-cyano-4-(2-methyl-3-trifluoromethyl-phenyl)-pyrrole of the formula

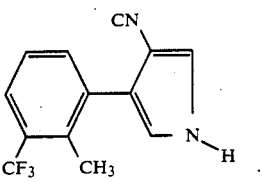

4. A fungicidal composition comprising a fungicidally effective amount of a compound according to claim 1 and a diluent.

5. A method of combating fungi which comprises applying to such fungi or to a fungus habitat a fungicidally effective amount of a compound according to claim 1.

6. A method of combating fungi which comprises applying to such fungi or to a fungus habitat a fungicidally effective amount of a compound according to claim 4.

* * * * *

UNITED STATES PATENT AND TRADEMARK OFFICE
CERTIFICATE OF CORRECTION

PATENT NO. : 5,091,408

DATED : February 25, 1992

INVENTOR(S) : Wollweber et al.

It is certified that error appears in the above-identified patent and that said Letters Patent is hereby corrected as shown below:

Col. 13, line 16   Delete " t " and substitute -- to --

Col. 14, line 19   Delete " claim 4 " and substitute -- claim 3 --

Signed and Sealed this

Fourteenth Day of September, 1993

Attest:

BRUCE LEHMAN

*Attesting Officer*    *Commissioner of Patents and Trademarks*